United States Patent
Peschard et al.

(10) Patent No.: US 10,668,000 B2
(45) Date of Patent: *Jun. 2, 2020

(54) PEPTIDES, COMPOSITIONS COMPRISING THEM AND USES IN PARTICULAR COSMETIC USES

(71) Applicant: SEDERMA, Le Perray en Yvelines (FR)

(72) Inventors: Olivier Peschard, Saint Prest (FR); Anne Doucet, Rambouillet (FR); Richard Leroux, Faverolles (FR); Philippe Mondon, Montrouge (FR)

(73) Assignee: SEDERMA, Le Perray En Yvelines (FR)

( * ) Notice: Subject to any disclaimer, the term of this patent is extended or adjusted under 35 U.S.C. 154(b) by 73 days.

This patent is subject to a terminal disclaimer.

(21) Appl. No.: 15/312,402

(22) PCT Filed: May 21, 2015

(86) PCT No.: PCT/IB2015/053737
§ 371 (c)(1),
(2) Date: Nov. 18, 2016

(87) PCT Pub. No.: WO2015/181688
PCT Pub. Date: Dec. 3, 2015

(65) Prior Publication Data
US 2017/0157014 A1 Jun. 8, 2017

(30) Foreign Application Priority Data
May 22, 2014 (FR) .................................... 14 54632

(51) Int. Cl.
| A61K 38/00 | (2006.01) |
| A61K 8/64 | (2006.01) |
| A61Q 19/08 | (2006.01) |
| C07K 5/097 | (2006.01) |

(52) U.S. Cl.
CPC ............... *A61K 8/64* (2013.01); *A61Q 19/08* (2013.01); *C07K 5/0823* (2013.01); *A61K 38/00* (2013.01); *A61K 2800/74* (2013.01)

(58) Field of Classification Search
None
See application file for complete search history.

(56) References Cited

U.S. PATENT DOCUMENTS

| 4,687,840 A * | 8/1987 | Pang ..................... C07K 5/0815 530/331 |
| 5,298,621 A * | 3/1994 | Marzi ................. C07K 5/06026 530/330 |
| 6,372,717 B1 | 4/2002 | Greff |
| 7,354,926 B2 | 4/2008 | Lintner |
| 2004/0115766 A1 | 6/2004 | Lintner |
| 2006/0165643 A1 | 7/2006 | Lintner |

(Continued)

FOREIGN PATENT DOCUMENTS

| EP | 0464009 | 6/1991 |
| FR | 2957252 | 9/2011 |
| WO | 9807744 | 2/1998 |
| WO | 02066668 | 8/2002 |
| WO | 2004012650 | 2/2004 |
| WO | 2004024695 | 3/2004 |
| WO | 2009104118 | 8/2009 |

(Continued)

OTHER PUBLICATIONS

Knipe (Organic Reaction Mechanisms 2007: An annual survey covering the literature dated Jan. to Dec. 2007, ISBN: 978-0-470-71238-2).*
Knipe (Organic Reaction Mechanisms 2007: An annual survey covering the literature dated Jan. to Dec. 2007, ISBN: 978-0-470-71238-2) (Year: 2007).*
Iwaniak et al. (Comprehensive Reviews in Food Science and Food Safety; 13; 114-134) (Year: 2014).*

(Continued)

*Primary Examiner* — Sergio Coffa
(74) *Attorney, Agent, or Firm* — RatnerPrestia

(57) ABSTRACT

The peptides have the general following formula: X-Pro*-Pro*-Xaa-Y in which: •Xaa is selected from Leucine (Leu, L), Arginine (Arg, R), Lysine (Lys, K), Alanine (Ala, A), Serine (Ser, S), and Aspartic acid (Asp, D); •At the N terminal end of the peptide, X is selected from H, —CO—R1 and —SO$_2$—R$_1$; •At the C terminal end of the peptide, Y is selected from OH, OR$_1$, NH$_2$, NHR$_1$ and NR$_1$R$_2$; •R$_1$ and R$_2$ are, independently from each other, selected from an alkyle, aryle, aralkyle, alkylaryl, alkoxy and aryloxy group, that can be linear, branched, cyclic, poly-cyclic, non-saturated, hydroxylated, carbonylated, phosphorylated and/or sulfured, and which skeletum can comprise an heteroatom, in particular an O, S and/or N atom; •Pro* correspond to a Proline, an analogue or derivative thereof; •if X is H then Y is selected from OR$_1$, NH$_2$, NHR$_1$ and NR$_1$R$_2$, and if Y is OH then X is —CO— or —SO$_2$—R$_1$; and the peptide hypoxanthine-Pro-Pro-Arg being excluded. The invention provides the use of the peptides of above formula I to stimulate the synthesis of the molecules constituting the dermal extracellular matrix, including collagen I and IV and elastin. A cosmetic treatment according to the invention includes anti-aging, anti-wrinkles, improving mechanical properties of the skin, firmness/tone/elasticity/suppleness/flexibility, increasing density and volume of the skin, restructuring effect, fighting stretch marks, improving skin barrier and/or skin hydration.

15 Claims, No Drawings
Specification includes a Sequence Listing.

(56) References Cited

U.S. PATENT DOCUMENTS

2011/0092431 A1* 4/2011 Ohsawa .............. C07K 5/0808
                                                    514/17.2
2011/0268812 A1   11/2011 Cauchard

FOREIGN PATENT DOCUMENTS

| WO | 2010067327 | 6/2010 |
| WO | 2010071132 | 6/2010 |
| WO | 2011125039 | 10/2011 |
| WO | 2012166810 | 12/2012 |
| WO | WO 2012/176172 | * 12/2012 |
| WO | 2013046137 | 4/2013 |
| WO | 2013105047 | 7/2013 |
| WO | 2013105048 | 7/2013 |

OTHER PUBLICATIONS

Zhang et al. (Curr Med Chem. 2012;19(11):1602-18) (Year: 2012).*
International Search report and Written Opinion for International Application No. PCT/IB2015/053737, dated May 21, 2015.

* cited by examiner

SEQUENCE LISTING

<160> NUMBER OF SEQ ID NOS: 23

<210> SEQ ID NO 1
<211> LENGTH: 5
<212> TYPE: PRT
<213> ORGANISM: artificial sequence

```
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 1

Lys Thr Thr Lys Ser
1               5

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 2

Gly Gln Pro Arg
1

<210> SEQ ID NO 3
<211> LENGTH: 5
<212> TYPE: PRT
<213> ORGANISM: Artificial sequence
<220> FEATURE:
<223> OTHER INFORMATION: synthetic peptide

<400> SEQUENCE: 3

Asn Ile Pro Pro Leu
1               5

<210> SEQ ID NO 4
<211> LENGTH: 4
<212> TYPE: PRT
<213> ORGANISM: Artificial sequence
<220> FEATURE:
<223> OTHER INFORMATION: synthetic peptide

<400> SEQUENCE: 4

Ile Pro Pro Leu
1

<210> SEQ ID NO 5
<211> LENGTH: 4
<212> TYPE: PRT
<213> ORGANISM: Artificial sequence
<220> FEATURE:
<223> OTHER INFORMATION: synthetic peptide

<400> SEQUENCE: 5

Val Pro Pro Phe
1

<210> SEQ ID NO 6
<211> LENGTH: 6
<212> TYPE: PRT
<213> ORGANISM: Artificial sequence
<220> FEATURE:
<223> OTHER INFORMATION: synthetic peptide

<400> SEQUENCE: 6

Pro Val Val Val Pro Pro
```

```
1               5
```

<210> SEQ ID NO 7
<211> LENGTH: 4
<212> TYPE: PRT
<213> ORGANISM: Artificial sequence
<220> FEATURE:
<223> OTHER INFORMATION: synthetic peptide

<400> SEQUENCE: 7

```
Phe Pro Pro Gln
1
```

<210> SEQ ID NO 8
<211> LENGTH: 4
<212> TYPE: PRT
<213> ORGANISM: Artificial sequence
<220> FEATURE:
<223> OTHER INFORMATION: synthetic peptide

<400> SEQUENCE: 8

```
Leu Pro Pro Thr
1
```

<210> SEQ ID NO 9
<211> LENGTH: 4
<212> TYPE: PRT
<213> ORGANISM: artificial sequence
<220> FEATURE:
<223> OTHER INFORMATION: synthetic peptide

<400> SEQUENCE: 9

```
Arg Ser Arg Lys
1
```

<210> SEQ ID NO 10
<211> LENGTH: 4
<212> TYPE: PRT
<213> ORGANISM: artificial sequence
<220> FEATURE:
<223> OTHER INFORMATION: synthetic peptide

<400> SEQUENCE: 10

```
Gly Gln Pro Arg
1
```

<210> SEQ ID NO 11
<211> LENGTH: 4
<212> TYPE: PRT
<213> ORGANISM: artificial sequence
<220> FEATURE:
<223> OTHER INFORMATION: synthetic peptide

<400> SEQUENCE: 11

```
Lys Thr Phe Lys
1
```

<210> SEQ ID NO 12
<211> LENGTH: 5
<212> TYPE: PRT
<213> ORGANISM: artificial sequence
<220> FEATURE:
<223> OTHER INFORMATION: synthetic peptide

<400> SEQUENCE: 12

```
Lys Thr Thr Lys Ser
1               5
```

```
<210> SEQ ID NO 13
<211> LENGTH: 6
<212> TYPE: PRT
<213> ORGANISM: artificial sequence
<220> FEATURE:
<223> OTHER INFORMATION: Synthetic peptide

<400> SEQUENCE: 13

Gly Lys Thr Thr Lys Ser
1               5

<210> SEQ ID NO 14
<211> LENGTH: 6
<212> TYPE: PRT
<213> ORGANISM: artificial sequence
<220> FEATURE:
<223> OTHER INFORMATION: synthetic peptide

<400> SEQUENCE: 14

Val Gly Val Ala Pro Gly
1               5

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by an Elaidoyl chain

<400> SEQUENCE: 15

Lys Thr Phe Lys
1

<210> SEQ ID NO 16
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain
<220> FEATURE:
<221> NAME/KEY: misc_feature
<222> LOCATION: (5)..(5)
<223> OTHER INFORMATION: Xaa can be any naturally occurring amino acid

<400> SEQUENCE: 16

Tyr Gly Gly Phe Xaa
1               5

<210> SEQ ID NO 17
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 17
```

```
Val Gly Val Ala Pro Gly
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 18

Gly Lys Thr Thr Lys Ser
1               5

<210> SEQ ID NO 19
<211> LENGTH: 6
<212> TYPE: PRT
<213> ORGANISM: artificial sequence
<220> FEATURE:
<223> OTHER INFORMATION: synthetic peptide

<400> SEQUENCE: 19

Glu Glu Met Gln Arg Arg
1               5

<210> SEQ ID NO 20
<211> LENGTH: 5
<212> TYPE: PRT
<213> ORGANISM: artificial sequence
<220> FEATURE:
<223> OTHER INFORMATION: synthetic peptide

<400> SEQUENCE: 20

Tyr Ala Gly Phe Leu
1               5

<210> SEQ ID NO 21
<211> LENGTH: 4
<212> TYPE: PRT
<213> ORGANISM: artificial sequence
<220> FEATURE:
<223> OTHER INFORMATION: synthetic peptide

<400> SEQUENCE: 21

Ala His Ser His
1

<210> SEQ ID NO 22
<211> LENGTH: 6
<212> TYPE: PRT
<213> ORGANISM: artificial sequence
<220> FEATURE:
<223> OTHER INFORMATION: synthetic peptide

<400> SEQUENCE: 22

Ser Ile Lys Val Ala Val
1               5

<210> SEQ ID NO 23
<211> LENGTH: 6
<212> TYPE: PRT
<213> ORGANISM: artificial sequence
<220> FEATURE:
<223> OTHER INFORMATION: synthetic peptide
```

```
<400> SEQUENCE: 23

Gly Pro Gln Gly Pro Gln
1               5
```

PEPTIDES, COMPOSITIONS COMPRISING THEM AND USES IN PARTICULAR COSMETIC USES

CROSS REFERENCE TO RELATED APPLICATIONS

This application is the National Stage filing of International Appln. No. PCT/IB2015/053737, filed 21 May 2015, and claims priority of French Application No. FR 1454632, filed 22 May 2014, the entire disclosures of which are incorporated herein by reference for all purposes.

TECHNICAL FIELD

The present invention relates to new peptides, compositions comprising them and therapeutical and cosmetic (oral and topic) uses. More particularly, the invention aims peptides for the treatment of skin and appendages, of human and animal mammals.

The invention concerns the cosmetic, hygiene and personal care, and dermopharmaceutical industries.

BACKGROUND ART

Peptides have an important signalling function and coordinate many biochemical processes. Therefore, peptides became essential and promising active ingredients especially in the cosmetic industry where compounds able to beautify the skin and its appendages, i.e. to improve their general condition, are always sought.

The present inventors were more particularly interested in searching for new peptides with activities on key molecules constituting the extracellular matrix (ECM) which decrease with age, particularly peptides active in the synthesis of collagen I and elastin and also active in the synthesis of glycoproteins like fibronectin.

Loss of density and thickness of the dermis is related to a reduction of the synthesis of macromolecules during aging by dermal fibroblasts, the cells responsible for their production. Collagen I is the most abundant protein in the dermis, essential to have a firm skin. Elastin is synthesized and secreted inside the dermal extracellular space. It is the major component of the elastic fibers (up to 90%).

Fibronectin is a glycoprotein present in the extracellular matrix, which plays a key role in cell adhesion to the extracellular matrix. It can simultaneously bind to the cell and to other molecules of the extracellular matrix, such as collagen or another molecule of fibronectin. Therefore, the molecules of fibronectin combine to form adhesive elastic fibers on the surface of many cells. This determines the mechanical properties (elasticity, flexibility, suppleness and firmness) of the skin.

The increase of collagen IV and laminins is also sought. It helps to restore/enhance the dermal/epidermal junction (DEJ). Collagen IV forms a two-dimensional network and is one of the major components of the DEJ. Laminins are also contained in the basal layer and involved in anchoring cells to the basal layer.

These two essential components of the DEJ provide together a better anchoring of the keratinocytes of the basal layer and help maintaining the flexibility and suppleness of the epidermis.

The reduction of protein synthesis with age becomes apparent at the level of the DEJ. Collagen IV is more fragmented and at the same time less produced, as well as laminins, which results in impaired JDE in some areas and poorer communication between melanocytes, keratinocytes and DEJ, and a reduced flexibility and suppleness of the system. The interest of stimulation of the synthesis of these two proteins thus clearly appears.

Results on the beautifying of skin and its general condition will be obtained thanks to the stimulation of the synthesis of these molecules, mainly results obtained at the level of the mechanical properties: a denser, more plumped, firmer, toned, supple and elastic skin, the peptide having a volumizing, plumping effect and thus an anti-wrinkle action.

Many peptides or peptide mixtures having properties on the MEC and anti-aging applications have been already proposed, including by the applicant, like the Pal-KTTKS (SEQ ID NO 1) marketed under the trademark MATRIXYL™, the mixture comprising Pal-GHK and Pal-GQPR (SEQ ID NO 2) under the trademark MATRIXYL™ 3000 or more recently the Pal-KMO2K under the tradename MATRIXYL Synthe-6™ (MO2 corresponding to a dioxygenated methionine). Other known peptides are mentioned in the following description.

Furthermore, patent application WO 2010/071132 discloses a series of eight peptides (-tri, -tetra, penta and hexa-peptides) derived from fermented milk and having been selected because they are not diggested by enzymes of the digestive tube and because they are able to penetrate the epithelial cells of the intestine. The authors further showed that at concentrations of about 40 ppm a stimulation of collagen synthesis and an increase in the proliferation of epidermal cells were observed. Due to these properties, the authors recommend that these peptides, naturally extracted or synthesized, could be advantageously ingested as oral cosmetics having anti-aging properties. The eight peptides have a PP (Pro-Pro) sequence: (Asn-Ile-Pro-Pro-Leu (NIPPL; SEQ ID NO 3), Ile-Pro-Pro (IPP), Ile-Pro-Pro-Leu (IPPL; SEQ ID NO 4), Val-Pro-Pro (VPP), Val-Pro-Pro-Phe (VPPF; SEQ ID NO 5), Pro-Val-Val-Val-Pro-Pro (PVVVPP; SEQ ID NO 6), Phe-Pro-Pro-Gln (FPPQ; SEQ ID NO 7) and Leu-Pro-Pro-Thr (LPPT; SEQ ID NO 8) and among them two peptides (the tetrapeptide IPPL (SEQ ID NO 4) and the pentapeptide NIPPL (SEQ ID NO 3)) comprise the more precise aminoacid sequence PPL. The NIPPL (SEQ ID NO 3) is presented as the prefered peptide with a better result in collagen production by fibroblastes: about +30% with regard to the control for a concentration of about 55 ppm, while only about +10% with regard to the control for a concentration of about 44 ppm for the IPPL peptide (SEQ ID NO 4).

EP 0 464 009 discloses oligopeptides derivatives of hypoxanthine and in particular the peptide hypoxanthine-PPR (hypoxanthine being the 6-hydroxypurine aralkyle radical) endowed with immunomodulating activity and pharmaceutical compositions containing them.

The aim of the present invention is to provide other peptides capable of improving the general condition of the skin and appendages, and more particularly peptides active on the synthesis of ECM proteins. In addition, it aims to provide sufficiently effective peptides that can be used alone or in combination, in amounts of a few ppm, and that can be used in the form of a topical composition, in particular a cosmetic composition.

SUMMARY OF THE INVENTION

According to a first subject matter the present invention provides peptides of the general following formula (I):

$$X\text{-Pro*-Pro*-Xaa-Y} \qquad (I)$$

Xaa being selected from Leucine (Leu, L), Arginine (Arg, R), Lysine (Lys, K), Alanine (Ala, A), Serine (Ser, S), and Aspartic acid (Asp, D);

At the N terminal end of the peptide, X being selected from H, —CO—$R_1$ and —$SO_2$—$R_1$;

At the C terminal end of the peptide, Y being selected from OH, $OR_1$, $NH_2$, $NHR_1$ and $NR_1R_2$, $R_1$ and $R_2$ being, independently from each other, selected from an alkyle, aryle, aralkyle, alkylaryl, alkoxy and aryloxy group, that can be linear, branched, cyclic, poly-cyclic, non-saturated, hydroxylated, carbonylated, phosphorylated and/or sulfured, and which skeletum can comprise an heteroatom, in particular an O, S and/or N atom;

Pro* corresponding to a Proline, an analogue or derivative thereof;

if X is H then Y is selected from $OR_1$, $NH_2$, $NHR_1$ and $NR_1R_2$, and if Y is OH then X is —CO—$R_1$ or —$SO_2$—$R_1$; and the peptide hypoxanthine-Pro-Pro-Arg being excluded of formula (I).

According to a second subject matter the present invention provides the use of at least one peptide of the general following formula:

X-Pro*-Pro*-Xaa-Y (I)

Xaa being selected from Leucine (Leu, L), Arginine (Arg, R), Lysine (Lys, K), Alanine (Ala, A), Serine (Ser, S), and Aspartic acid (Asp, D);

At the N terminal end of the peptide, X being selected from H, —CO—$R_1$ and —$SO_2$—$R_1$;

At the C terminal end of the peptide, Y being selected from OH, $OR_1$, $NH_2$, $NHR_1$ and $NR_1R_2$;

$R_1$ and $R_2$ being, independently from each other, selected from an alkyle, aryle, aralkyle, alkylaryl, alkoxy and aryloxy group, that can be linear, branched, cyclic, poly-cyclic, non-saturated, hydroxylated, carbonylated, phosphorylated and/or sulfured, and which skeletum can comprise an heteroatom, in particular an O, S and/or N atom;

Pro* corresponding to a Proline, an analogue or derivative thereof; and if X is H then Y is selected from $OR_1$, $NH_2$, $NHR_1$ and $NR_1R_2$, and if Y is OH then X is —CO—$R_1$ or —$SO_2$—$R_1$;

or a topical composition comprising said at least one peptide in a physiologically acceptable medium for a non therapeutical cosmetic treatment.

The detailed description of in vitro evaluations given below shows that the peptides of the invention are active on the marker molecules of the ECM, active as from a few ppm, and can be used alone or in mixture to improve the appearance and the general state of the skin and its appendages, and in particular for the treatment and/or prevention of the signs of aging, and/or of skin and its appendages imperfections. The inventors have in particular shown that the peptides of the invention exhibit a procollagen activity, especially with regard to collagen 1 and collagen 4 and a pro-elastin activity. Advantageously also, the peptides of the present invention exhibit keratinocyte differentiation properties which allows to consider an activity at the epiderm level (moisturizing, strengthening the skin barrier). This activity also complements a global anti-aging activity.

The present invention encompasses the following derivatives or analogues of proline:

1) Resulting from different ring size (for example 4 or 6 bonds);

2) Resulting from the change of the relative position (α or β) of the acid function (COOH) with respect to the nitrogen of the ring.

3) Resulting from substitutions on the cycle that change its size and/or polarity.

4) Resulting from the combination of the above items.

They can be represented by the following general formula II:

In any position

Formula II

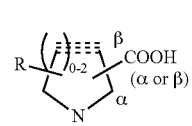

The present invention provides preferably the following analogue compounds presented in table 1 having a nitrogen atom in the cycle like the proline (A 5 atom ring and COOH in α):

| Compound name | Chemical structure |
|---|---|
| azetidine-2-carboxylic acid | 4 atom ring and COOH in α |
| β-proline (or pyrrolidine-3-carboxylic acid) | 5 atom ring and COOH in β |
| pipecolic acid | 6 atom ring and COOH in α |
| nipecotic acid | 6 atom ring and COOH in β |
| thio-proline (or thiazolidine-4-carboxylic acid) | 5 atom ring and COOH in α + S in position 4 |
| 4-hydroxy-proline | 5 atom ring and COOH in α + OH in position 4 |
| 3,4-dehydro-proline | 5 atom ring and COOH in α + 3-4 insaturation |

Other compounds resulting from the substitution of the proline by an R group are also possible. Non limitative examples are given in the following table 2:

| R group | Position |
|---|---|
| piperidin-4-yl | 1 on the nitrogen |
| phenyl; dimethyl | 3 |
| phenyl; OH; $NH_2$; F; $F_2$; $CF_3$; benzyl; cyclohexyl; oxo; bromobenzyl; SH; phenoxy | 4 |
| phenyl; dimethyl; oxo | 5 |
| phenyl, cyclohexyl | 4 + 5 |

Proline can also by replaced by substituted analogues having a 6 bond ring as in the examples given in the following table 3:

| Compound name | Chemical structure |
|---|---|
| 3-carboxy-morpholine | Oxygenated 6 bond ring + COOH in position 3 |
| 2-carboxy-morpholine | Oxygenated 6 bond ring + COOH i position 2 |
| Tic (or 1,2,3,4-tetrahydro-isoquinoline-3-carboxylic acid) and its hydroxylated derivative | 6 bond ring + COOH in position 2 on this ring + phenyl in position 4 + 5 |
| Tiq (or 1,2,3,4-tetrahydro isoquinoline-1-carboxylic acid) | 6 bond ring + COOH in position 6 on this ring + indole in position 4 + 5 |

According to the invention, in formula I, if X is H then Y is selected from $OR_1$, $NH_2$, $NHR_1$ and $NR_1R_2$, and if Y is OH then X is —CO—$R_1$ or —$SO_2$—$R_1$; peptides having in formula I, X=H and Y=OH are excluded in particular to favor peptides having a substitution on the N-terminal or C-terminal end because such peptides have a better biodisponibility (cutaneaous penetration power enhanced).

According to the invention, in formula I, preferably:
Pro* is Proline, the natural aminoacid; and/or
Xaa is selected from Leucine (Leu, L) and Arginine (Arg, R).

Therefore, two prefered peptides according to the invention are X-PPL-Y and X-PPR-Y.

According to other preferred features of the invention:
$R_1$ and/or $R_2$ is an alkyl chain of 1 to 24 carbon atoms, preferably a lipophilic alkyl chain of 3 to 24 carbon atom; and/or
X is an acyle group CO—$R_1$ and Y is selected from OH, OMe, OEt and $NH_2$, preferably OH; X is preferably selected from octanoyle ($C_8$), decanoyle ($C_{10}$), lauroyl ($C_{12}$), myristoyle ($C_{14}$), palmitoyle ($C_{16}$), stearoyle ($C_{18}$), biotinoyle, elaidoyle, oleoyle and lipoyle; more preferably selected from lauroyle ($C_{12}$), myristoyle ($C_{14}$) and palmitoyle ($C_{16}$); and/or
Y is OH and X is selected from palmitoyle ($C_{16}$), myristoyle ($C_{14}$) and lauroyle ($C_{12}$); more preferably myristoyle ($C_{14}$).

Prefered peptides according to the invention are Myr-PPL-OH and Myr-PPR-OH. As can be seen in the detailed description below, these two peptides are capable of acting on the synthesis of the most important molecules of dermis (collagen I and IV, fibronectine, laminins and elastin) and for Myr-PPL-OH of epidermis (keratinocyte differentiation).

The peptides of the invention may be optically pure, or be made of L- or D-isomers or a mixture thereof. L isomers which are those found in nature may be preferred.

The peptides may be in the form of salts, especially hydrochloride salt.

The present invention also covers derivatives (with modification and/or addition of a chemical function but without change in the carbon skeleton) and analogues (with modification and/or addition of a chemical function but with an additional change in the skeleton atoms), complexes with other species such as a metal ion (eg copper, zinc, manganese, magnesium, and others).

The present invention also provides a composition, in particular topical, comprising at least one peptide according to the invention in a physiologically acceptable medium. According to the medium (forming the so-called excipient) and the peptide dosage this composition will form for example a concentrated active ingredient or a final composition less concentrated directly aiming the client or patient.

"Physiologically acceptable medium" means according to the present invention, without limitation, an aqueous or hydro-alcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, nails, scalp, hair and body hair, and skin of mammals, particularly human, compositions which may be ingested or injected into the skin, without risk of toxicity, incompatibility, instability, allergic response, and others. This "physiologically acceptable medium" forms what is commonly called the excipient of the composition.

The peptides of the invention can be solubilized in a hydrophilic or lipophilic matrix with optionally a solubilizer, depending on the future use.

The peptides may be associated with other active ingredients at effective concentrations to act synergistically or in reinforcement to achieve the desired effects described for the invention, such as the following agents: anti-aging, anti fine lines and wrinkles, lightening, pro-pigmenting, moisturizers, humectants, slimming, anti-acne, anti-inflammatory, anti-oxidants, acting on skin radiance, anti-glycation, volumizing, restructurizers, anti-carbonylation, dermo-relaxants, anti-hair regrowth, acting on the stratum corneum, on the dermal-epidermal junction, on the production of HSPs proteins, on firmness, elasticity, tone of skin, hair growth (eyelashes, eyebrows for example), etc.

The composition according to the invention may be applied to the face, body, neckline, scalp, hair, eyelashes, body hair, in whatever form or vehicles known to those skilled in the art, especially in the form of a solution, dispersion, emulsion, paste or powder, individually or in a premix, or be vehiculed individually or in premix by vectors such as macrocapsules, microcapsules or nanocapsules, macrospheres, microspheres or nanospheres, liposomes, oleosomes or chylomicrons, macroparticles, microparticles or nanoparticles, macrosponges, microsponges or nanosponges, microemulsions or nanoemulsions, or adsorbed on powdery organic polymers, talcs, bentonites, spores or exines and other inorganic or organic materials.

In cosmetics in particular, applications can be proposed for example in skin care product ranges for the face, body or hair, and in care and make-up ranges, including eyelashes and eyebrows.

In general, the peptides according to the present invention may be used in any form whatsoever, in a form bound to or incorporated in or absorbed in or adsorbed on macro-, micro-, and nanoparticles, or macro-, micro-, and nanocapsules, for the treatment of textiles, natural or synthetic fibers, wools, and any materials that may be used for clothing or underwear for day or night intended to come into contact with the skin, handkerchiefs or cloths, to exert their cosmetic effect via this skin/textile contact and to permit continuous topical delivery.

The CTFA International cosmetic ingredient dictionary & handbook (15th Ed. 2014) (published by the Cosmetic, Toiletry, and Fragrance Combination, Inc., Washington, D.C.) describes a non-limited wide variety of cosmetic and pharmaceutical ingredients conventionally used in the skin care industry that can be used as additional ingredients in the compositions of the present invention. Further skin care and hair care active ingredients that are particularly useful combined with the composition can be found in SEDERMA commercial literature and on the websites www.sederma.fr and www.sederma.com.

The following commercial actives can also be mentioned, as examples: betain, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (trade name of the acetyl hexapeptide-3 of Lipotec), spilanthol or an extract of *Acmella oleracea* known under the name Gatuline Expression™, an extract of *Boswellia serrata* known under the name Boswellin™, Deepaline PVB™ (Seppic), Syn-AKE™ (Pentapharm), Ameliox™, Bioxilift™ (Silab), Phyto-CellTec™ Argan (Mibelle), Papilactyl D™ (Silab), Prevenhelia™ (Lipotec), Subliskin™ (Sederma), Venuceane™ (Sederma), Moist 24™ (Sederma), Vegesome Moist 24™ (Sederma), Essenskin™ (Sederma), Juvinity™ (Sederma), Revidrat™ (Sederma), Resistem™ (Sederma), Chronodyn™ (Sederma), Kombuchka™ (Sederma), Chromocare™ (Sederma), Calmosensine™ (Sederma), Glycokin factor S™ (Sederma), Biobustyl™ (Sederma), Idealift™ (Sederma), Ceramide 2™, Ceramide A2™ et Ceramide HO3™ (Sederma), Odawhite™ (Sederma), Lumisphere™ (Sederma), Legance™ (Sederma), Intenslim™ (Sederma), Zingerslim™, (Sederma), Prodizia™ (Sederma), Beautifeye™ (Sederma), Senestem™ (Sederma), Meiritage™ (Sederma), Senestem™ (Sederma), Sebuless™ (Sederma), Pacifeel™ (Sederma), Majestem™ (Sederma), NG Shea Unsaponifiable™ (Sederma) or mixtures thereof.

Among other plant extracts which can be combined with the composition of the invention, there may more particularly be mentioned extracts of Ivy, in particular English Ivy (*Hedera Helix*), of *Bupleurum chinensis*, of *Bupleurum falcatum*, of *Arnica* (*Arnica montana* L), of Rosemary (*Rosmarinus officinalis* N), of Marigold (*Calendula officinalis*), of Sage (*Salvia officinalis* L), of Ginseng (*Panax ginseng*), of *Zingiber zerumbet* sm., of Ginko Biloba, of St.-John's-Wort (*Hyperycum perforatum*), of Butcher's-broom (*Ruscus aculeatus* L), of European meadowsweet (*Filipendula ulmaria* L), of big-flowered Jarva tea (*Orthosiphon stamincus benth*), of algae (*Fucus vesiculosus*), of Birch (*Betula alba*), of green tea, of cola nuts (*Cola nipida*), of Horse-chestnut, of bamboo, of *Centella asiatica*, of Heather, of Fucus, of Willow, of Mouse-ear, of Escine, of Cangzhu, of *chrysanthellum indicum*, of the plants of the *Armeniacea* genus, *Atractylodis platicodon*, *Sinnomenum*, *Pharbitidis*, *Flemingia*, of *Coleus* such as *C. forskohlii*, *C. blumei, C. esquirolii, C. scutellaroides, C. xanthantus* and *C. barbatus*, such as the extract of root of *Coleus barbatus*, extracts of *Ballote*, of *Guioa*, of *Davallia*, of *Terminalia*, of *Barringtonia*, of *Trema*, of *antirobia, cecropia, argania, dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia cordifolia*), and Guggal (extracted from plants of the genus *Commiphora*, particularly *Commiphora mukul*), kola extract, chamomile, red clover extract, *Piper methysticum* extract (Kava Kava™ from SEDERMA), *Bacopa monieri* extract (Bacocalmine™ from SEDERMA) and sea whip extract, extracts of *Glycyrrhiza glabra*, of mulberry, of *melaleuca* (tea tree), of *Larrea divaricata*, of *Rabdosia rubescens*, of *Euglena gracilis*, of *Fibraurea recisa Hirudinea*, of *Chaparral sorghum*, of sun flower extract, of *Enantia chlorantha*, of Mitracarpe of *Spermacocea* genus, of *Buchu barosma*, of *Lawsonia inermis* L., of *Adiantum capillus-veneris* L., of *Chelidonium majus*, of *Luffa cylindrica*, of Japanese Mandarin (*Citrus reticulata blanco* var. *unshiu*), of *Camelia sinensis*, of *Imperata cylindrica*, of *Glaucium flavum*, of *Cupressus sempervirens*, of *Polygonatum multiflorum*, of *loveyly hemsleya*, of *Sambucus nigra*, of *Phaseolus lunatus*, of *Centaurium*, of *Macrocystis pyrifera*, of *Turnera diffusa*, of *Anemarrhena asphodeloides*, of *Portulaca pilosa*, of *Humulus lupulus*, of *Coffea arabica*, of *Ilex paraguariensis*, or of *Globularia cordifolia*, of *Albizzia julibrissin*, of *Oxydendron* arboretum, of *Zingimber zerumbet smith*, of *Astragalus membranaceus*, of *Bupleurum falcatum* of *Atractylodes macrocephalae*, of *Plantago lanceolata, Leontopodium alpinum* or *Apium graveolens*.

The compositions of the present invention may include other peptides, including, without limitation, the di-, tri-, tetra-, penta- and hexapeptides and derivatives thereof. According to a particular embodiment, the concentration of the additional peptide, in the composition, ranges from $1 \times 10^{-7}\%$ and 20%, preferably from $1 \times 10^{-6}\%$ and 10%, preferably between $1 \times 10^{-5}\%$ and 5% by weight. According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (beta-AH), YR, VW, NF, DF, KT, KC, CK, KP, KK or TT. Suitable tripeptides for use herein include, but are not limited to RKR, HGG, GHK, GKH, GGH, GHG, KFK, KPK, KMOK, $KMO_2K$ or KAvaK. Suitable tetrapeptides for use herein include but are not limited to RSRK (SEQ ID NO 9), GQPR (SEQ ID NO 10) or KTFK (SEQ ID NO 11). Suitable pentapeptides include, but are not limited to KTTKS (SEQ ID NO 12). Suitable hexapeptides include but are not limited to GKTTKS (SEQ ID NO 13) and VGVAPG (SEQ ID NO 14).

Other suitable peptides for use herein include, but are not limited to: lipophilic derivatives of peptides, preferably myristoyl and palmitoyl derivatives, and metal complexes as aforementioned (e.g. copper complex of the tripeptide HGG). Preferred dipeptide include for example N-Palmitoyl-beta-Ala-His, N-Acetyl-Tyr-Arg-hexadecylester (Calmosensine™, Idealift™ from Sederma), Pal-KT or Pal-RT (Sederma). Preferred tripeptide derivatives include for example N-Palmitoyl-Gly-Lys-His, and Pal-Gly-His-Lys, (Pal-GKH and Pal-GHK from Sederma), the copper derivative of HGG (Lamin™ from Sigma), Lipospondin (N-Elaidoyl-KFK) and its analogs of conservative substitution, N-Acetyl-RKR-$NH_2$ (Peptide CK+), N-Biot-GHK (from Sederma), Pal-$KMO_2K$ (Matrixyl Synthe6™ from Sederma) and derivatives thereof. Suitable tetrapeptide derivatives for use according to the present invention include, but are not limited to, N-Pal-GQPR (SEQ ID NO 2) (from Sederma) and Ela-KTFK (SEQ ID NO 15). Suitable pentapeptide derivatives for use herein include, but are not limited to, N-Pal-KTTKS (SEQ ID NO 1) (available as Matrixyl™ from Sederma), Pal-YGGF-X (SEQ ID NO 16) with X Met or Leu or mixtures thereof. Suitable hexapeptide derivatives for use herein include, but are not limited to, Pal-VGVAPG (SEQ ID NO 17) and Pal-GKTTKS (SEQ ID NO 18) and derivatives thereof. The mixture of Pal-GHK and Pal-GQPR (SEQ ID NO 2) (Matrixyl™ 3000, Sederma) can also be mentioned.

The preferred compositions commercially available containing a tripeptide or a derivative include Biopeptide-CL™, Maxilip™, Biobustyl™, Procapil™ and Matrixyl™synthe'6™ of Sederma. The compositions commercially available preferred sources of tetrapeptides include Rigin™, Eyeliss™ Matrixyl™ Reloaded and Matrixyl 3000™ which contain between 50 and 500 ppm of Pal-GQPR (SEQ ID NO 2) and an excipient, proposed by Sederma.

The following commercially available peptides can be mentioned as well as additional active ingredients:

Vialox™ (INCI name=Pentapeptide-3 (synthetic peptide comprising alanine, arginine, isoleucine, glycine and proline)), Syn-Ake™ (β-Ala-Pro-Dab-NH-Bzl) or Syn-Coll™ (Pal-Lys-Val-Lys-OH) marketed by Pentapharm;

Argireline™ (Ac-Glu-Glu-Met-Gln-Arg-Arg-NH$_2$ (INCI name=Acetyl hexapeptide-3) (SEQ ID NO 19), Leuphasyl™ (Tyr-D-Ala-Gly-Phe-Leu) (SEQ ID NO 20), Aldenine™ (Gly-His-Lys), Trylagen™ (INCI name=Pseudoalteromonas Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-β-Ala-His-Ser-His)(SEQ ID NO 21), Serilesine™ (Ser-Ile-Lys-Val-Ala-Val) (SEQ ID NO 22), Decorinyl™ (INCI name: Tripeptide-10 Citrulline=reaction product of Citrulline and Tripeptide-10 (synthetic peptide constituted of aspartic acid, isoleucine and lysine) or Preventhelia™ (reaction product of 2,3-diaminopropionic acid and Tripeptide-33 (synthetic peptide comprising Alanine, Histidine and proline)) marketed by Lipotec;

Collaxyl™ (Gly-Pro-Gln-Gly-Pro-Gln (SEQ ID NO 23)) or Quintescine™ (Cys-Gly) marketed by Vincience;

Cytokinol™LS (casein hydrolysate) marketed by Les Laboratoires Serobiologiques/Cognis;

Kollaren™ (Gly-His-Lys), IP2000™ (Pal-Val-Tyr-Val) or Meliprene™ (INCI name=Monofluoroheptapeptide-1: reaction product of acetic ace and a synthetic peptide comprising arginine, glycine, glutamic acid, histidine, norleucine, p-fluorophenylalanine and tryptophan) marketed by l'Institut Europeen de Biologie Cellulaire;

Neutrazen™ (Pal-His-D-Phe-Arg-NH$_2$) marketed by Innovations; or

BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) marketed by Infinitec Activos.

Hydroxyprolisilane CN™ INCI Name: Methylsilanol Hydroxyproline Aspartate (Exsymol); or ECM-Protect™ INCI name: Dextran (and) VYV; (Lucas Meyer Cosmetics).

The present invention also provides a topical cosmetic or therapeutic treatment method for improving the appearance and general state of the skin and its appendages, comprising the topical application to the skin of a subject in need thereof of an effective amount of a peptide or a mixture of peptides according to the invention or a composition comprising according to the invention comprising said peptide or mixture of peptides, said peptides being as recited above.

« Topical treatment » or "topical use" means according to the invention, an application that is intended to act where it is applied: skin, mucosa and/or appendages.

A cosmetic treatment is directed to a normal and healthy skin.

The peptide or composition of the invention may be applied locally to the targeted areas.

The "effective" amount depends on various factors, such as age, the state of the subject, the severity of the disorder or condition and mode of administration. An effective amount means a nontoxic amount sufficient to produce the desired effect.

In a cosmetic composition according to the invention, the peptides to be present in an effective amount are generally in proportions of between 0.000001% and 15% relative to the total weight of the composition, more preferably between 0.0001% and 5%, depending on the destination of the composition and the more or less pronounced desired effect. The peptides may be present in the compositions according to the invention in varying relative proportions, in equivalent amounts, or on the contrary in different proportions.

All percentages and ratios used herein are by weight of the total composition and all measurements are made at 25° C. unless it is otherwise specified.

For example, for a face cosmetic treatment, the European Cosmetics Directive has set a standard amount for applying a cream of 2.72 mg/cm$^2$/day/person and for a body lotion of 0.5 mg/cm$^2$/day/person.

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a peptide or a mixture of peptides of the invention, and in a second compartment a composition containing another active ingredient and/or excipient, the compositions contained in the said first and second compartments in this case being considered to be a combination composition for simultaneous, separate or stepwise use in time, particularly in one of the treatment methods recited above.

The treatment method according to the invention is more particularly adapted to slow down degradation of the molecules of the dermal extracellular matrix and/or act on the DEJ via stimulation of collagen IV and/or laminins, more particularly adapted to the following treatments:

Global antiaging; and/or

Anti-fine lines and wrinkles (skin relief smoothed; wrinkles filled), and/or

Improvement of mechanical properties of the skin: firmness/elasticity/flexibility/suppleness/tone, and/or Increasing of density and volume of skin (volumizing and pumpling effect), and/or Restructuring effect, Fighting stretchmarks, For improving skin barrier, and/or For skin hydration/moisturizing.

Other applications are of course conceivable for the peptides of the invention (alone or combined), for example slimming, detoxifying, anti-glycation, antioxidant, tensing, anti-fatigue, anti-undereye bags and/or dark circles, calming, hair growth, skin radiance, pigmentation, scalp, etc., with a preventive and/or curative action.

A composition according to the invention, comprising at least one of the peptides encompassed by formula I, is suitable for the therapeutic treatment of a diseased skin deficient in molecules constituting the dermal extracellular matrix.

DETAILED DESCRIPTION

The present invention will be better understood and other features will appear in the light of the following non limiting examples.

A) Example of Preparation of a Peptide According to the Invention: The Myr-PPL-OH The Myr-PPL-OH peptide is prepared by peptidic synthesis. Leucine is coupled with a resin via its terminal acid function (with a coupling agent such as DCC (dicyclohexylcarbodiimide)/NHS (N-hydroxysuccinimide) or HBTU (2-(1H-benzotriazole-1-yl)-1,1,3,3-tetramethyluronium hexafluorophosphate)/HOBT (1-hydroxy-benzotriazole)). Leucine thus protected is reacted with a derivative of proline in the presence of a coupling agent. The same operation is then realized to add the second proline. The latter is thereafter acylated on its amine with an activated derivative of myristic acid (myristoyle chloride for example) in the presence of a base. After precipitation, washing and drying, myristoyl-prolyl-prolyl-leucine product is obtained in a solid form.

This same synthesis method can be applied to other peptides of formula I according to the invention, for example to the Myr-PPR-OH peptide.

B) Preparation of a Composition According to the Invention Comprising the Myr-PPL-OH Peptide of Example A)

Starting Materials:
  The pur peptide, synthesized according to the synthesis method explained above;
  Excipient: a mixture of fatty esters, chosen to form an oily matrix, for example for forming a composition without water for the further formulation of cosmetic formulation free of water.
Operating Mode:
  The peptide is mixed to the excipient and put under gentle stirring and heating until solubilization and total clarity.

C) In Vitro Evaluations

The peptides of the invention have a number of remarkable effects presented below. Peptides prepared according to A) above and dissolved in an excipient were tested in vitro and showed the activities that are presented below.

1) ELISA Assays

Protocol

Normal human fibroblasts (NHF) in culture are contacted with the products to be tested or their excipient (negative control) for 72 h. After the contact, the culture supernatants are removed and the synthesis of dermal macromolecules are estimated by ELISA assays. An estimation of cell viability is performed by Hoechst assay and used to weight the obtained data.

Results

TABLE 4

| Collagen I | | | |
|---|---|---|---|
| Compound | Concentration | % change/ control | Significance (Student test) |
| Myr-PPA-OH | 3 ppm | +40 | $p < 0.05$ |
| Myr-PPA-OH | 7 ppm | +143 | $p < 0.01$ |
| Myr-PPS-OH | 3 ppm | +70 | $p < 0.01$ |
| Myr-PPS-OH | 7 ppm | +172 | $p < 0.01$ |
| Myr-PPD-OH | 1 ppm | +27 | $p < 0.05$ |
| Myr-PPD-OH | 3 ppm | +57 | $p < 0.01$ |
| Myr-PPD-OH | 7 ppm | +44 | $p < 0.01$ |
| Myr-PPK-OH | 3 ppm | +75 | $p < 0.01$ |
| Myr-PPK-OH | 4 ppm | +68 | $p < 0.05$ |

TABLE 4-continued

| Collagen I | | | |
|---|---|---|---|
| Compound | Concentration | % change/ control | Significance (Student test) |
| Myr-PPK-OH | 5 ppm | +145 | $p < 0.01$ |
| Myr-PPL-OH | 1 ppm | +34 | $p < 0.05$ |
| Myr-PPL-OH | 3 ppm | +59 | $p < 0.01$ |
| Myr-PPL-OH | 5 ppm | +87 | $p < 0.01$ |
| Myr-PPR-OH | 3 ppm | +90 | $p < 0.01$ |
| Myr-PPR-OH | 4 ppm | +163 | $p < 0.01$ |
| Myr-PPR-OH | 5 ppm | +160 | $p < 0.01$ |

TABLE 5

| Collagen IV | | | |
|---|---|---|---|
| Compound | Concentration | % change/ control | Significance (Student test) |
| Myr-PPA-OH | 7 ppm | +54 | $p < 0.05$ |
| Myr-PPS-OH | 3 ppm | +28 | $p < 0.01$ |
| Myr-PPS-OH | 7 ppm | +42 | $p < 0.01$ |
| Myr-PPD-OH | 1 ppm | +23 | $p < 0.01$ |
| Myr-PPD-OH | 3 ppm | +37 | $p < 0.01$ |
| Myr-PPK-OH | 3 ppm | +37 | $p < 0.05$ |
| Myr-PPK-OH | 4 ppm | +52 | $p < 0.01$ |
| Myr-PPK-OH | 5 ppm | +64 | $p < 0.01$ |
| Myr-PPK-OH | 6 ppm | +57 | $p < 0.01$ |
| Myr-PPL-OH | 1 ppm | +38 | $p < 0.01$ |
| Myr-PPL-OH | 3 ppm | +51 | $p < 0.01$ |
| Myr-PPL-OH | 5 ppm | +83 | $p < 0.01$ |
| Myr-PPL-OH | 7 ppm | +159 | $p < 0.01$ |
| Myr-PPR-OH | 3 ppm | +49 | $p < 0.01$ |
| Myr-PPR-OH | 4 ppm | +64 | $p < 0.01$ |
| Myr-PPR-OH | 5 ppm | +104 | $p < 0.01$ |
| Myr-PPR-OH | 6 ppm | +93 | $p < 0.01$ |

TABLE 6

| Fibronectin | | | |
|---|---|---|---|
| Compound | Concentration | % change/ control | Significance (Student test) |
| Myr-PPA-OH | 1 ppm | +25 | $p < 0.05$ |
| Myr-PPA-OH | 7 ppm | +60 | $p < 0.01$ |
| Myr-PPS-OH | 1 ppm | +28 | $p < 0.01$ |
| Myr-PPS-OH | 7 ppm | +87 | $p < 0.01$ |
| Myr-PPD-OH | 1 ppm | +53 | $p < 0.01$ |
| Myr-PPD-OH | 3 ppm | +44 | $p < 0.01$ |
| Myr-PPD-OH | 7 ppm | +48 | $p < 0.01$ |
| Myr-PPK-OH | 3 ppm | +32 | $p < 0.05$ |
| Myr-PPK-OH | 5 ppm | +46 | $p < 0.01$ |
| Myr-PPL-OH | 3 ppm | +73 | $p < 0.01$ |
| Myr-PPL-OH | 5 ppm | +41 | $p < 0.05$ |
| Myr-PPL-OH | 7 ppm | +66 | $p < 0.01$ |
| Myr-PPR-OH | 4 ppm | +27 | $p < 0.01$ |

TABLE 7

| Laminin | | | |
|---|---|---|---|
| Compound | Concentration | % change/ control | Significance (Student test) |
| Myr-PPA-OH | 1 ppm | +40 | $p < 0.05$ |
| Myr-PPA-OH | 3 ppm | +80 | $p < 0.01$ |
| Myr-PPA-OH | 7 ppm | +143 | $p < 0.01$ |
| Myr-PPS-OH | 7 ppm | +41 | $p < 0.01$ |
| Myr-PPD-OH | 3 ppm | +23 | $p < 0.05$ |
| Myr-PPK-OH | 1 ppm | +34 | $p < 0.05$ |
| Myr-PPK-OH | 3 ppm | +102 | $p < 0.01$ |

TABLE 7-continued

Laminin

| Compound | Concentration | % change/control | Significance (Student test) |
|---|---|---|---|
| Myr-PPK-OH | 5 ppm | +92 | p < 0.01 |
| Myr-PPL-OH | 1 ppm | +29 | p < 0.05 |
| Myr-PPL-OH | 3 ppm | +83 | p < 0.01 |
| Myr-PPL-OH | 5 ppm | +53 | p < 0.01 |
| Myr-PPL-OH | 7 ppm | +41 | p < 0.05 |
| Myr-PPR-OH | 3 ppm | +24 | p < 0.01 |
| Myr-PPR-OH | 4 ppm | +39 | p < 0.01 |

TABLE 8

Elastin

| Compound | Concentration | % change/control | Significance (Student test) |
|---|---|---|---|
| Myr-PPA-OH | 7 ppm | +57 | p < 0.05 |
| Myr-PPA-OH | 10 ppm | +92 | p < 0.01 |
| Myr-PPS-OH | 3 ppm | +60 | p < 0.05 |
| Myr-PPS-OH | 7 ppm | +117 | p < 0.01 |
| Myr-PPD-OH | 1 ppm | +63 | p < 0.01 |
| Myr-PPD-OH | 3 ppm | +65 | p < 0.01 |
| Myr-PPD-OH | 7 ppm | +123 | p < 0.01 |
| Myr-PPD-OH | 10 ppm | +85 | p < 0.05 |
| Myr-PPK-OH | 3 ppm | +46 | p < 0.05 |
| Myr-PPL-OH | 5 ppm | +86 | p < 0.05 |
| Myr-PPL-OH | 7 ppm | +137 | p < 0.01 |
| Myr-PPR-OH | 5 ppm | +81 | p < 0.01 |

The results show that the peptides according to the invention stimulate the synthesis of collagens I and IV, fibronectin, laminins and elastin on normal human fibroblasts at concentrations of a few ppm and in significant amounts, with a predominant activity for Myr-PPR-OH and Myr-PPL-OH.

2) Immunofluorescence Dosages

Protocol

Normal human fibroblasts (NHF) are cultured for 24 h. The cells are contacted or not with the products to be tested or their excipient at various concentrations for 6 days for the collagen I or 14 days for elastin (DMEMc 5% FCS). The synthesis of collagen I and elastin produced by the cells in the form of extracellular matrix is then quantified by immuno-marking on the fixed layers. A counting of the nuclei labeled with Hoechst is performed in parallel in order to have an estimate of the viability and in order to weight the data.

Results

TABLE 9

Collagen I

| Compound | Concentration | % change/control | Significance (U Mann Whitney test) |
|---|---|---|---|
| Myr-PPL-OH | 3 ppm | +68 | p < 0.01 |
| Myr-PPL-OH | 7 ppm | +95 | p < 0.01 |

TABLE 10

Elastin

| Compound | Concentration | % change/control | Significance (U Mann Whitney test) |
|---|---|---|---|
| Myr-PPL-OH | 2 ppm | +183 | p < 0.01 |
| Myr-PPL-OH | 3 ppm | +259 | p < 0.01 |
| Myr-PPL-OH | 7 ppm | +145 | p < 0.01 |
| Myr-PPR-OH | 2 ppm | +148 | p < 0.01 |
| Myr-PPR-OH | 3 ppm | +141 | p < 0.01 |
| Myr-PPR-OH | 7 ppm | +44 | p < 0.01 |

3) Keratinocyte Differentiation a. Visual Effect

Protocol

Human keratinocytes are brought to just confluence in KSFMc medium. The contact with the actives and therefore their evaluation is then done in KSFMc medium alone or with calcium (0.8 mm)*. Visual evaluation of differentiation takes place after several days of contact (2, 4, 8 days/3, 5 and 7 for example).

* Calcium differentiation allows the creation of link structure between the cells which leads to a better attachment of the basal layers.

Results

| Peptide | Keratinocyte differenciation |
|---|---|
| Pal-KTTKS - positive control | + at 5 ppm |
| Myr-PPL-OH | ++ at 5 ppm | b. Marking of Neutral Lipids with Red Oil

Protocol

On the same cultures as presented before, a marking of neutral lipids with red oil is realised on the fixed layers. Quantification by image analysis is used to estimate lipid synthesis in keratinocytes. A counter-colouration of the nucleus using Hoechst dye is used to weight the obtained data.

Results

| Peptide | Concentration | % variation |
|---|---|---|
| Myr-PPL-OH | 4 ppm | +394 (p < 0.01) |
|  | 6 ppm | +570 (p < 0.01) |

The results show that the peptide Myr-PPL-OH increases the neutral lipids in the human keratinocytes (at the level of the differentiation networks).

c. Filaggrin 1 and Ceramide 2 Immunolabeling

Protocol

On the same cultures as those presented before, immunolabeling of filaggrin 1 and ceramides are realised on layers fixed with specific antibodies. Quantification by image analysis is used to estimate the synthesis of these targets in keratinocytes. A counter-colouration of the nucleus using Hoechst dye is used to weight the obtained data.

Results

| Peptide | Concentration | Filagrin 1 % variation | Ceramide 2 % variation |
|---|---|---|---|
| Myr-PPL-OH | 2 ppm | +564 (p < 0.01) | +137 (nsd) |
|  | 4 ppm | +840 (p < 0.01) | +240 (p < 0.01) |
|  | 6 ppm | +172 (p < 0.01) | +268 (p < 0.01) |

The results show that the peptide Myr-PPL-OH increases filaggrin 1 and ceramides in the human keratinocytes (at the level of the differentiation networks).

These results show that the peptide of the invention, and in particular the Myr-PPL-OH, have a pro-differentiating potential on keratinocytes and can be used to improve the properties of the epidermis and skin barrier, in particular for a skin hydration topical treatment.

A) Galenic

Different formulations are described below. Additional cosmetic active ingredients, in support and/or in complement of the activity of the active ingredient of invention, can be added to the appropriate phase according to their hydrophobic or hydrophilic nature. These ingredients can be of any class according to their(s) function(s), place of application (body, face, neck, chest, hands, hair, eyelashes, eyebrows, body hair, etc.), the desired final effect, and the targeted consumer, for example antioxidant, moisturizing, nourishing, protective, smoothing, remodeling, volumizing, lipofiling, acting on the radiance of the complexion, anti-spots, anti-dark circles, anti-glycation, slimming, soothing, myo-relaxant, anti-redness, anti-stretch marks, etc. They are mentioned above in the description.

1) Cream Form, in Particular an Anti-Aging Day Cream for Face

| Ingredient (INCI name) | Weight % |
|---|---|
| Phase A | |
| Sorbitan Stearate | 3.00 |
| Cyclopentasiloxane (and) Cyclohexasiloxane | 2.00 |
| Ethylhexyl Palmitate | 3.00 |
| Glyceryl Stearate (and) PEG-100 Stearate | 3.00 |
| Ethylhexyl Methoxycinnamate | 1.00 |
| Ethylhexyl Dimethyl PABA | 1.00 |
| Phase B | |
| Demineralised water | Qsp 100 |
| Ultrez 10 (Carbomer) | 0.40 |
| Phase C | |
| Glycerin | 5.00 |
| Conservative | qs |
| Phase D | |
| Peptide according to the invention in a fatty excipient | 3.00 |
| Phase E | |
| Potassium Sorbate | 0.10 |
| Phase F | |
| Sodium Hydroxide 30% | 0.60 |
| Demineralised water | 6.00 |
| Phase G | |
| Perfume | 0.10 |

Protocol:

Weigh phase A and heat to 75° C. in a water bath. Weigh phase B and let rise for 20 minutes. Melt phase C until dissolved and add to phase B. Heat phase (B+C) to 75° C. in a water bath. Pour phase A into phase (B+C) under Staro stirring. Extemporaneously, add phase D to phase (A+B+C). At approximately 45° C. add phase E and neutralize with phase F. Mix well. At 35° C., add G. Homogenize well. pH: 6.20.

Examples of Ingredients that can be Added to this Formulation:

CALMOSENSINE™: soothing active for sensitive skins marketed by Sederma (WO1998/07744) comprising the lipo-dipeptide Tyr-Arg. It reduces discomfort feelings.

SEBULESS™: purifying sebo-regulator ingredient comprising a *Syringa vulgaris* extract, marketed by Sederma, which mattifies and refreshes complexion, fades the inflammatory blemishes.

PRODIZIA™: active ingredient marketed by Sederma (WO2013/046137), comprising an extract of *Albizia julibrissin*, fighting the signs cutaneous fatigue: dark circles, under eye bags, dull complexion and drawn features, by repairing and protection the skin against the caused by damages of glycation.

PACIFEEL™: active ingredient actif marketed by Sederma, comprising a natural extract of the *Mirabilis jalapa* plant also known as the Marvel of Peru, which alleviates cutaneous discomfort, fades redness of sensitive and reactive skin and strengthens and hydrates the epidermis.

2) Gel Form, for Example a Firming Gel for the Body

| Ingredient (INCI name) | Weight % |
|---|---|
| Phase A | |
| Demineralised water | Qsp 100 |
| Ultrez 10 (Carbomer) | 0.20 |
| Phase B | |
| PEG 400 | 5.00 |
| Conservatives | qs |
| Phase C | |
| Dimethicone | 4.00 |
| Pemulen TR2 (Acrylates/C10-30 Alkyl Acrylate Cross Polymer) | 0.20 |
| Phase D | |
| Tween 20 (Polysorbate 20) | 1.00 |
| Peptide of the invention in a fatty excipient | 2.00 |
| Phase E | |
| Potassium Sorbate | 0.10 |
| Phase F | |
| Sodium Hydroxide 30% | 0.60 |
| Demineralised water | 5.00 |
| Phase G | |
| Perfume | 0.10 |

Protocol:

Disperse Ultrez 10 in water and let swell for 15 minutes. Heat phase B until dissolved and add to phase A. Weigh and mix phase C. Mix phase D and add to phase C; homogenise well. Add phase (C+D) to phase (A+B). Then add phase E. Let swell for 1 hour. Homogenise well. Neutralize with phase F. Finally, add G. pH 6.10.

Examples of Ingredients that can be Added to this Formulation:

AQUALANCE™: osmo-protector moisturising active ingredient marketed by Sederma (WO2009/104118) comprising homarine and erythritol.

LEGANCE™: anti-aging active marketed by Sederma (WO2013/105047), corresponding to a *Zingiber zerumbet* Smith extract obtained by $CO_2$ supercritical in a water-soluble excipient and titrated in zerumbone ingredient. It is a global anti-aging ingredient for legs. It improves their appearance and comfort by reducing water retention, improving microcirculation and refining adipose tissue.

BODYFIT™: slimming/firming active ingredient comprising glaucine marketed by Sederma (WO 2004/024695). BODYFIT™ reduces the appearance of cellulite and helps to improve drainage and water distribution in the tissues.

JUVINITY™: active marketed by Sederma (WO 2011/125039) reducing signs of aging on the face and neckline, smoothing wrinkles, densifying and restructuring the dermis.

3) Compact Powder Form

| Ingredient (INCI name) | Weight % |
|---|---|
| Phase A | |
| Talc | Qsp 100 |
| Kaolin | 2.00 |
| Calcium Stearate | 1.00 |
| Mica | 4.00 |
| Silica | 1.00 |
| Bismuth Oxychloride | 2.00 |
| Potassium Sorbate | qs |
| Phenoxyethanol | qs |
| Phase B | |
| Unipure Black LC 989 HLC [CI 77499 (and) Hydrogenated Lecithin] | 0.20 |
| Unipure Red LC 381 HLC [CI 77491 (and) Hydrogenated Lecithin] | 0.60 |
| Unipure Yellow LC 182 HLC [CI 77492 (and) Hydrogenated Lecithin] | 1.00 |
| Covapearl Star Gold 2302 AS [CI 77891 (and) CI 77491 (and) Synthetic Fluorphlogopite (and) Triethoxycaprylylsilane] | 0.50 |
| Covapearl Brown 838 HLC [CI 77491 (and) Mica (and) Hydrogenated Lecithin) | 1.00 |
| Covapearl Dark Blue 637 [CI 77510 (&) CI 77891 (&) Mica] | 0.10 |
| Phase C | |
| Crodamol PTIS-LQ-(MV) [Pentaerythrityl Tetraisostearate] | 4.00 |
| Peptide of the invention in an oily matrix | 3.00 |
| Phase D | |
| Perfume | 0.30 |

Protocol:

Weigh phase A and mix. Weigh phase B and pour into phase A. Pour phase A+B into the blender and blend. Add phase C to A+B in several times and mix each time. Add phase D. Check homogeneity at each step.

Example of Ingredient that can be Added to this Formulation:

VEGESOME MOIST 24™: ingredient marketed by Sederma designed for the formulation of moisturizing powder makeup; it is a powder consisting of hollow particles 25 microns (*Lycopodium clavatum* exins) loaded with an *Imperata cylindrica* extract having moisturizing properties.

4) Alternative Cream Form (Face or Body)

| Ingredient (INCI name) | Weight % |
|---|---|
| Phase A | |
| Arlacel 170 (Glyceryl Stearate (and) PEG-100 Stearate) | 5.50 |
| Abil Wax 2434 (Stearoxy Dimethicone) | 3.00 |
| Acetulan (Cetyl Acetate (and) Acetylated Lanolin Alcohol) | 1.50 |
| Crodacol C 90 (Cetyl Alcohol) | 1.50 |
| Mineral Oil | 3.00 |
| Shea Butter | 5.00 |
| Unsaponifiable Shea | 1.00 |
| Parsol MCX (Ethylhexyl Methoxicinnamate) | 3.50 |
| Phase B | |
| Demineralised Water | Qs 100 |
| Phase C | |
| Carbopol 940 (Carbomer) | 0.20 |
| Phase D | |
| Demineralised Water | 2.00 |
| Triethanolamine 99% | 0.20 |
| Phase E | |
| Propylene Glycol | 0.10 |
| Mixed Parabens | |
| Phase F | |
| Sodium Hydroxide 30% | 5.00 |
| Demineralised Water | qs |
| Phase G | |
| Peptide of the invention in a lipophilic medium | 2.00 |

Protocol:

Weigh phase A and heat to 75° C. in a water bath. Weigh phase B and let swell for 20 minutes. Melt phase C until dissolved and add to phase B. Heat phase (B+C) to 75° C. in a water bath. Pour phase A into phase (B+C) under Staro stirring. Extemporaneously, add phase D to phase (A+B+C). At approximately 45° C. add phase E and neutralize with phase F. Homogenise well. At 35° C., add G. Homogenise well. pH: 6.20.

Examples of Ingredients that can be Added to this Formulation:

SUBLISKIN™: active ingredient marketed by Sederma (WO2010/067327) that moisturizes and smooths the skin while allowing it to resist to external aggressions.

VENUCEANE™: active marketed by Sederma (WO2002/066668) comprising a *Thermus thermophiles* biotechnological extract, that prevents visible signs of photo-aging (spots, wrinkles, dryness . . . ), protects cell structures from damages caused by UV and strengthens skin integrity.

KOMBUCHKA™: active ingredient acting on complexion marketed by Sederma (WO2004/012650).

INTENSLIM™: slimming active ingredient marketed by Sederma (WO2013/105048) corresponding to a synergistic combination of extracts obtained by *Globularia cordifolia* plant cell culture, *Zingiber zerumbet* Smith titrated in zerumbone and vegetable caffeine obtained by supercritical $CO_2$ extraction.

The invention claimed is:

1. A topical composition comprising:
   an amount of between 0.000001% and 15%, relative to the total weight of the composition, of at least one peptide of the general following formula:

X-Pro*-Pro*-Xaa-Y      (I)

Xaa is selected from Leucine (Leu, L), Arginine (Arg, R), Lysine (Lys, K), Alanine (Ala, A), Serine (Ser, S), and Aspartic acid (Asp, D);
   at the N terminal end of the peptide, X is an acyl group CO—$R_1$ selected from octanoyl ($C_8$), decanoyl ($C_{10}$), lauroyl ($C_{12}$), myristoyl ($C_{14}$), palmitoyl ($C_{16}$), stearoyl ($C_{18}$), biotinoyl, elaidoyl, oleoyl and lipoyl;
   at the C terminal end of the peptide, Y is selected from OH, $OR_1$, $NH_2$, $NHR_1$ and $NR_1R_2$;
   $R_1$ and $R_2$, independently from each other, are selected from an alkyl, aryl, aralkyl, alkylaryl, alkoxy and aryloxy group, that can be linear, branched, cyclic, poly-cyclic, non-saturated, hydroxylated, carbonylated, phosphorylated and/or sulfured, and which backbone can comprise an heteroatom;
   Pro* is a Proline, an analogue or derivative thereof; and
   a physiologically acceptable topical medium for a non-therapeutic cosmetic treatment or for a therapeutic treatment.

2. The topical composition according to claim 1, wherein in formula I, Pro* is Proline.

3. The topical composition according to claim 1, wherein Xaa is selected from Leucine (Leu, L) and Arginine (Arg, R), the peptide being X-PPL-Y or X-PPR-Y.

4. The topical composition according to claim 1, wherein $R_2$ is an alkyl chain of 1 to 24 carbon atoms.

5. The topical composition according to claim 1, wherein $R_1$ and/or $R_2$ is an alkyl chain of 1 to 24 carbon atoms.

6. The topical composition according to claim 1, wherein Y is selected from OH, OMe, OEt and $NH_2$.

7. The topical composition according to claim 6, wherein Y is OH.

8. The topical composition according to claim 1, wherein X is selected from myristoyl ($C_{14}$) and palmitoyl ($C_{16}$).

9. The topical composition according to claim 8, wherein X is myristoyl.

10. The topical composition according to claim 9, wherein the peptide is selected from Myr-PPL-OH and Myr-PPR-OH.

11. The topical composition according to claim 1, wherein the backbone of $R_1$ and/or $R_2$ comprises a heteroatom selected from O, S, and N.

12. A method for a therapeutical treatment of a skin deficient in molecules constituting the dermal extracellular matrix, comprising applying to the skin of a person in need thereof the topical composition according to claim 1 to stimulate synthesis of at least one molecular constituting the dermal extracellular matrix, wherein each Pro* is proline and Y is OH.

13. A method for a topical cosmetic treatment, comprising applying a topical composition according to claim 1 to skin, wherein each Pro* is proline and Y is OH.

14. The method according to claim 13, wherein the topical cosmetic treatment is an anti-ageing treatment.

15. The method according to claim 13, wherein the topical cosmetic treatment is a treatment:
   Of wrinkles and fine lines, and/or
   For ameliorating the mechanical properties of skin, firming, toning, elasticity, flexibility and suppleness, and/or
   For increasing the density and volume of skin (volumating or re-pulping effect), and/or
   For restructuring skin,
   For fighting strechmarks,
   For improving skin barrier, and/or
   For skin hydration.

* * * * *

UNITED STATES PATENT AND TRADEMARK OFFICE
CERTIFICATE OF CORRECTION

PATENT NO.         : 10,668,000 B2
APPLICATION NO.    : 15/312402
DATED              : June 2, 2020
INVENTOR(S)        : Olivier Peschard et al.

Page 1 of 1

It is certified that error appears in the above-identified patent and that said Letters Patent is hereby corrected as shown below:

On the Title Page

Item [72], Inventors:
"Olivier Peschard, Saint Prest (FR)" should read --Olivier Peschard, Rambouillet (FR)--

Signed and Sealed this
Fourteenth Day of July, 2020

Andrei Iancu
*Director of the United States Patent and Trademark Office*